(12) United States Patent
Donovan et al.

(10) Patent No.: US 11,236,234 B2
(45) Date of Patent: Feb. 1, 2022

(54) JOINT COMPOUNDS AND PLASTERS WITH A COMPLEXOMETRIC DYE AND METHODS

(71) Applicant: United States Gypsum Company, Chicago, IL (US)

(72) Inventors: Alexander Donovan, Glencoe, IL (US); Joseph Schlude, South Barrington, IL (US)

(73) Assignee: UNITED STATES GYPSUM COMPANY, Chicago, IL (US)

(*) Notice: Subject to any disclaimer, the term of this patent is extended or adjusted under 35 U.S.C. 154(b) by 24 days.

(21) Appl. No.: 15/860,819

(22) Filed: Jan. 3, 2018

(65) Prior Publication Data
US 2019/0203050 A1  Jul. 4, 2019

(51) Int. Cl.
| | | |
|---|---|---|
| C09B 29/14 | (2006.01) | |
| C04B 28/14 | (2006.01) | |
| C07C 309/50 | (2006.01) | |
| C09B 29/16 | (2006.01) | |
| C07C 303/22 | (2006.01) | |
| G01N 31/22 | (2006.01) | |
| C04B 111/00 | (2006.01) | |
| C04B 103/00 | (2006.01) | |

(52) U.S. Cl.
CPC ............. *C09B 29/14* (2013.01); *C04B 28/14* (2013.01); *C07C 303/22* (2013.01); *C07C 309/50* (2013.01); *C09B 29/16* (2013.01); *G01N 31/222* (2013.01); *C04B 2103/0086* (2013.01); *C04B 2111/00681* (2013.01); *C04B 2111/00689* (2013.01)

(58) Field of Classification Search
CPC ......... C09B 29/14; C09B 29/16; C04B 28/14; C04B 2103/0086; C04B 2111/00681; C04B 2111/00689; C07C 303/22; C07C 309/50; G01N 31/222
See application file for complete search history.

(56) References Cited

U.S. PATENT DOCUMENTS

| | | | |
|---|---|---|---|
| 2,082,887 A | 6/1937 | Haydon | |
| 2,678,280 A | 5/1954 | Noyes et al. | |
| 2,910,349 A * | 10/1959 | Reeder | G01N 31/22 436/79 |
| 4,524,828 A | 6/1985 | Sabins et al. | |
| 4,661,161 A | 4/1987 | Jakacki et al. | |
| 5,746,822 A | 5/1998 | Espinoza et al. | |
| 6,476,099 B1 | 11/2002 | Cimaglio et al. | |
| 6,531,528 B1 * | 3/2003 | Kurp | C04B 26/06 524/291 |
| 6,545,066 B1 | 4/2003 | Immordino, Jr. et al. | |
| 6,663,979 B2 | 12/2003 | Deodhar et al. | |
| 6,805,741 B1 | 10/2004 | Liu et al. | |
| 7,594,963 B2 | 9/2009 | Bonetto et al. | |
| 8,323,785 B2 | 12/2012 | Yu et al. | |
| 9,040,612 B2 | 5/2015 | Brandon et al. | |
| 9,174,881 B2 | 11/2015 | Cimaglio et al. | |
| 9,328,023 B2 | 5/2016 | Rosenthal et al. | |
| 9,751,812 B2 | 9/2017 | Bowers et al. | |
| 2005/0064175 A1 | 3/2005 | Azari et al. | |
| 2007/0167325 A1 | 7/2007 | Leroux | |
| 2008/0004176 A1 | 1/2008 | Cullen et al. | |
| 2009/0229196 A1 | 9/2009 | Tubervile | |
| 2010/0038598 A1 | 2/2010 | Bastiaansen et al. | |
| 2010/0225988 A1 | 9/2010 | Kalkanoglu et al. | |
| 2011/0050756 A1 | 3/2011 | Cassidy et al. | |
| 2011/0100844 A1 * | 5/2011 | Cimaglio | C04B 28/14 206/219 |
| 2011/0141336 A1 | 6/2011 | Mittleman | |
| 2011/0170162 A1 | 7/2011 | Briancon et al. | |
| 2012/0109071 A1 | 5/2012 | Larsen et al. | |
| 2013/0104797 A1 | 5/2013 | Chiappo | |
| 2016/0066894 A1 | 3/2016 | Barton-Sweeney | |
| 2016/0079178 A1 | 3/2016 | Kim | |
| 2016/0106880 A1 | 4/2016 | Coomber | |
| 2016/0303275 A1 | 10/2016 | Joseph et al. | |

FOREIGN PATENT DOCUMENTS

| | | |
|---|---|---|
| CN | 103387523 A | 11/2013 |
| CN | 105136785 A | 12/2015 |
| DE | 202006005022 U1 | 7/2006 |
| WO | WO2000066508 A3 | 11/2000 |
| WO | WO03026883 A1 | 4/2003 |
| WO | WO2008003672 A1 | 1/2008 |
| WO | WO2008091184 A1 | 7/2008 |
| WO | WO2010058346 A2 | 5/2010 |
| WO | 2011096925 A1 | 8/2011 |
| WO | WO2017050619 A9 | 3/2017 |

OTHER PUBLICATIONS

Ross et al. ("Indicator Reagents" in Ullmann's Encyclopedia of Industrial Chemistry, Jun. 15, 2000, p. 1-27).*
Patton et al. ("New Indicator for Titration of Calcium with (Ethylenedinitrilo) Tetraacetate", Anal. Chem., 1956, 28, 6, p. 1026-1026).*
Search report received in Chilean Application No. 202001581, dated Sep. 20, 2021.

* cited by examiner

*Primary Examiner* — Robert H Havlin
(74) *Attorney, Agent, or Firm* — Greer, Burns & Crain, Ltd.; Philip T. Petti; Pradip Sahu

(57) ABSTRACT

A building construction product comprising an ionochromic dye, wherein the building construction product has a first color when the product comprises water, wherein the first color is dependent on the presence of metal ions in solution in the product; and wherein the product has a second color when the product has solidified. Methods of monitoring setting and drying reactions of building construction products, including setting-type and drying-type joint compounds and plasters.

7 Claims, 4 Drawing Sheets

JOINT COMPOUNDS AND PLASTERS WITH A COMPLEXOMETRIC DYE AND METHODS

TECHNICAL FIELD

This invention relates to building construction products including joint compounds, coatings, paints, gypsum slurries and plasters comprising an indicator, and methods for making, storing and applying these products.

BACKGROUND

Joint compounds are commonly used in various construction projects, including for building a wall partition, ceiling and other assemblies. One of the applications for a joint compound is to fill in a seam between two gypsum panels from which a wall is constructed. A great variety of other applications includes patching wall defects and cracks.

Two types of joint compounds are known: a setting-type joint compound and a drying-type joint compound. Often, a setting-type joint compound comprises calcium sulfate hemihydrate (also known as plaster of Paris or calcined gypsum). The setting-type joint compounds set via a setting reaction in which calcium sulfate hemihydrate hydrates into calcium sulfate dihydrate (gypsum). This results in hardening of the setting-type joint compound. Setting-type joint compounds include those described in U.S. Pat. Nos. 4,661,161, 5,746,822, 6,805,741 and 9,174,881, which are incorporated herein by reference.

A setting-type joint compound can be formulated as a dry powder which is mixed with water prior to its application. Adding water to the dry powder initiates conversion of calcined gypsum into gypsum, which triggers setting and hardening of the joint compound.

A setting-type joint compound can be also formulated as a wet setting-type joint compound in the ready-mixed state. Examples of such compounds are provided in U.S. Pat. No. 9,174,881. Such compounds are already pre-mixed with water, yet can be stored on a shelf for a period of time without setting and hardening. In order to inhibit the setting reaction during storage and transportation, the wet ready-mixed setting-type joint compounds contain a retarder which is a chelator that binds calcium ions and prevents a re-hydration reaction of calcined gypsum. An activator is then added to a ready-mixed setting-type joint compound in order to release the calcium ions and initiate a setting reaction.

Various activators are known, including zinc sulfate, iron sulfate and aluminum sulfate, as provided in U.S. Pat. No. 5,746,822, also incorporated herein by reference.

Unlike setting-type joint compounds, drying-type joint compounds are not formulated with calcined gypsum. Drying-type joint compounds solidify when water evaporates and the compounds transition from an aqueous state into a solid compound. Many drying-type joint compounds comprise calcium carbonate. Drying-type joint compounds include those provided in U.S. Pat. Nos. 6,476,099, 6,545,066 and 9,328,023, the disclosures of which are incorporated herein by reference.

Plaster, which can be formulated with calcined gypsum and water, is a building material which may be used as a protective and/or decorative coating on walls, ceilings or other structures to form a smooth hard surface when plaster paste sets and hardens. Plaster formulations include those provided by U.S. Pat. No. 2,082,887, which is incorporated herein by reference.

Various coatings, including primer coatings, formulated with gypsum and/or calcium carbonate are also available on the market. Examples of coatings include those provided in U.S. Pat. No. 6,663,979, which is incorporated herein by reference. A water-based gypsum slurry is used for making wallboard and other types of gypsum panels and tiles. Examples of gypsum panels include those provided in U.S. Pat. No. 8,323,785, incorporated herein by reference.

After an application of a setting-type joint compound, an operator may benefit from an indicator and/or test that allows the operator to determine accurately whether the applied product has fully set. This may prevent a mistake of subsequent application before the previously applied product had fully set. Setting indicators may be also useful in plasters, coatings and gypsum, slurries. With products such as drying-type joint compounds, an operator needs an indicator/test that determines accurately whether the drying joint compound has fully dried.

U.S. Pat. No. 6,531,528 provides a ready to use patch and repair product that includes a color change indicator such as phenolphthalein (red) and thymolphthalein (blue). The compounds are pH indicators which change their color dependent on changes in pH.

Yet, accurate indicators are still needed which would not necessarily depend on a pH of a setting or drying product because not all products can be accurately monitored, based on changes in pH.

SUMMARY

These and some other needs are addressed at least in part by this disclosure which provides a building construction product comprising an ionochromic dye. The building construction product has a first color when the product comprises water, the first color being dependent on the presence of metal ions in solution in the product. The product has a second color when the product has solidified. The building construction product may be a gypsum slurry, plaster or a setting-type joint compound and the ionochromic dye comprises calconcarboxylic acid. The ionochromic dye may comprise calconcarboxylic acid coated on a carrier. The building construction product may be a ready-mixed setting-type joint compound which comprises a retarder and the ionochromic dye comprises calconcarboxylic acid. The building construction product may be a drying-type joint compound. The building construction product may be a drying-type joint compound which comprises a calcium compound and the ionochromic dye comprises calconcarboxylic acid. The building construction product may be a ready-mixed drying-type joint compound which comprises a calcium compound and the ionochromic dye comprises calconcarboxylic acid. The building construction product may be a drying-type joint compound which comprises a calcium carbonate and the ionochromic dye comprises calconcarboxylic acid. The building construction product may comprise metal ions including, but not limited to, ionic calcium, ionic magnesium, ionic aluminum, ionic ferrous, ionic ferric, ionic cuprous, ionic cupric, ionic bismuth, and/or ionic zinc.

Further aspects of this disclosure provide a method of applying a building construction product which comprises water. The method comprises mixing the building construction product with an ionochromic dye and thereby obtaining a mixture of the building construction product comprising an indicator, wherein the mixture develops a first color, and wherein the development of the first color is dependent on the presence of metal ions. This method may be performed with a setting-type joint compound, drying-type joint compound, plaster, coating, primer coating, gypsum slurry or paint. In some application of the method, the building construction product is a setting-type joint compound, plaster or gypsum slurry and the ionochromic dye comprises a reversible chelator of calcium ions. The building construction product may be a setting-type joint compound, plaster or gypsum slurry and the ionochromic dye may comprise calconcarboxylic acid. The method may be performed with a ready-mixed setting-type joint compound which comprises a retarder, and the ionochromic dye may be mixed with the ready-mixed setting-type joint compound during at least one of the following time periods: (a) prior to application and (b) at the time of application. The method may further comprise mixing the ready-mixed setting-type joint compound with at least one activator at the time of application. The method may be performed with a drying-type joint compound which comprises a calcium compound and the ionochromic dye comprises a reversible chelator of calcium ions. The method may be performed with a ready-mixed drying-type joint compound which comprises a calcium compound and the ionochromic dye comprises calconcarboxylic acid.

Further aspects of this disclosure include a method for monitoring a ready-mixed setting joint compound, the method comprising formulating the ready-mixed setting joint compound with at least one ionochromic dye which comprises a reversible chelator of calcium ions and monitoring the compound for a change in color, wherein the change in color is indicative of premature activation of a setting reaction.

This disclosure also provides an accessory product comprising an ionochromic dye which comprises a reversible chelator of calcium ions and optionally further comprising a solvent, wherein the accessory product is provided in a package in a form of a container or a pouch, and wherein the amount of the ionochromic dye is dosed per the package. In preferred embodiments, the accessory product comprises calconcarboxylic acid coated on a carrier.

DETAILED DESCRIPTION

Figure 1:
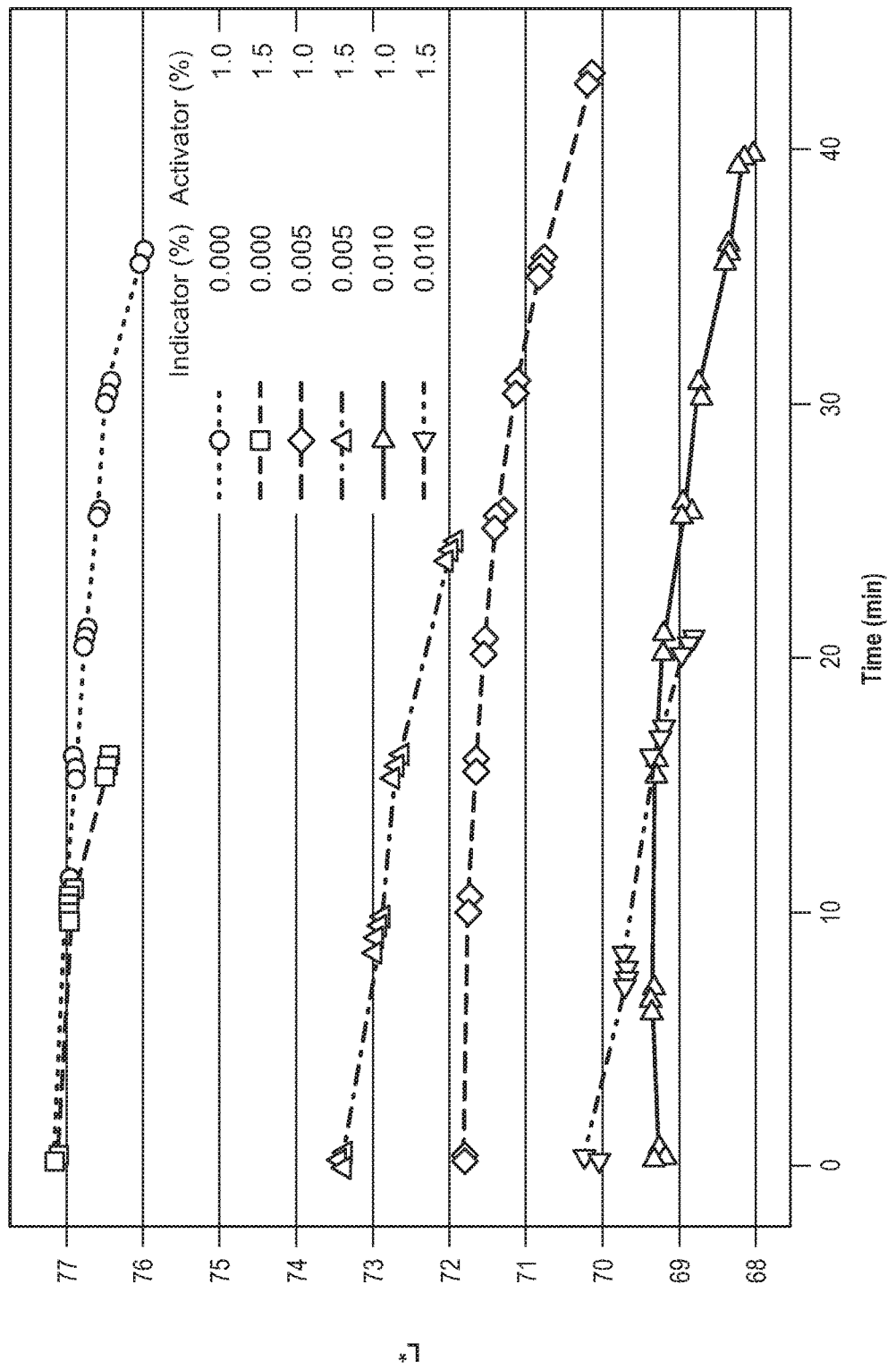
FIG. 1 are graphs of L* value as a function of time for a setting-type joint compound in a ready-mixed state with varying amounts of an indicator and activator.

This disclosure provides building construction products including joint compounds, coatings, paints, gypsum slurries and plasters, which comprise an indicator. The product has a first color in the presence of water. The product changes its color once the product has hardened. Thus, the indicator monitors a setting reaction in a product which sets by rehydration of calcined gypsum. The indicator also monitors a drying reaction of a drying product comprising metal ions.

The indicator is a complexometric (i.e. ionochromic) dye which changes its color based on the presence or absence of free metal ions such as calcium ions in a setting or drying product.

The term "indicator" is used in this disclosure broadly, and includes a complexometric (i.e. ionochromic) dye which changes its color depending on the amount of metal ions in a solution.

Ionochoromic dyes are analytical chemistry reagents employed in complexometric titrations to determine an ionic metal concentration in samples of interest. An ionochromic dye is an ionsensitive molecule which manifests abrupt chromic transitions by changes in color. The indicator may be an ionochromic dye which changes its color dependent on the presence and concentration of at least one from ionic calcium, ionic magnesium, ionic aluminum, ionic iron (ferrous and/or ferric), ionic copper (cuprous and/or cupric), ionic bismuth, or ionic zinc. A preferred indication is an ionochromic dye which changes its color dependent on the presence and concentration of ionic calcium.

A particularly preferred indicator is a reagent comprising calconcarboxylic acid and/or its salt and/or its derivative. Suitable salts of calconcarboxylic acid include sodium salt of calconcarboxylic acid.

Calconcarboxylic acid is also referred to as the Patton-Reeder indicator (CAS ID Number 3737-95-6). It has the following structural formula (I):

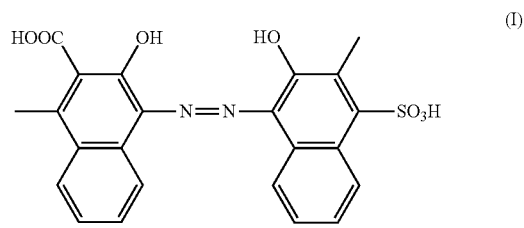 [SMILES: Cc1c(O)c(N=Nc2c(O)c(C(=O)O)c(C)c3ccccc23)c2ccccc2c1S(=O)(=O)O]

(I)

Calconcarboxylic acid is a dark purple to almost black powder that is sparingly soluble in water. It may be mixed with sodium sulfate and is used in conjunction with EDTA in calcium titration experiments under alkaline conditions. Calconcarboxylic acid appears red in aqueous calcium solutions and blue otherwise. Calconcarboxylic acid is a weak and reversible chelator of ionic calcium. Calconcarboxylic acid may be used to measure the ionic calcium concentration of aqueous solutions and solid samples. In some embodiments, solid samples must be first solubilized in an alkaline solution to produce a color change with a chelator.

Other suitable indicators include complexometric compounds which complex with at least one metal ion in a colorimetric reaction which produces a detectable change in color. In the products of this disclosure, the presence of calcium ions and/or other metal ions is detected with the indicator.

Suitable indicators which are used together with or instead of calconcarboxylic acid, its salts and derivatives include reagents listed in Table 1, their salts and derivatives. Any indicator in Table 1 may be used in combination with any other indicator in addition or instead of the compound with formula (I).

TABLE 1

| Indicator | CAS ID Number | Other Names | Manufacturer |
| --- | --- | --- | --- |
| Alizarin | 72-48-0 | Mordant Red 11 and Turkey Red | Sigma Aldrich |

TABLE 1-continued

| Indicator | CAS ID Number | Other Names | Manufacturer |
|---|---|---|---|
| Arsenazo III | 1668-00-4 | | Sigma Aldrich |
| ERIOCHROME<sup>R</sup> Blue Black R | 2538-85-4 | Mordant Black 17 | LabChem |
| ERIOCHROME<sup>R</sup> Black T | 1787-61-7 | Mordant Black 11 and Solochrome Black | Sigma Aldrich |
| ERIOCHROME<sup>R</sup> Red B | 3618-63-1 | | Fisher Chemical |
| Murexide | 3051-09-0 | ammonium purpurate | Sigma Aldrich |
| CALMAGITE<sup>R</sup> | 3147-14-6 | | Sigma Aldrich |
| Hydroxynaphthol Blue | 63451-35-4 | | Fisher Chemical |
| SPADNS | 23647-14-5 | | ACROS Organics |
| Calcichrome | 3810-39-7 | | Pfaltz & Bauer |
| MAGON | 523-67-1 | | TCI America |
| Magneson | 74-39-5 | azo violet | Alfa Aesar |
| Phenazo | 3687-26-1 | | Angene International |
| Catechol-violet | 115-41-3 | | Sigma Aldrich |
| Thymol blue | 76-61-9 | | Fisher Chemical |
| Curcumin | 458-37-7 | | Sigma Aldrich |
| Fast Sulphon Black F | 3682-47-1 | | ACROS Organics |
| Xylenol orange | 1611-35-4 | | TCI America |
| Xylenol orange tetrasodium salt | 3618-43-7 | | Sigma Aldrich |
| Calcein | 1461-15-0 | Fluorexon | MP Biomedicals |
| Calcein blue | 54375-47-2 | | Sigma Aldrich |
| Zincon | 135-52-4 | | Angene International |
| Zincon sodium salt | 62625-22-3 | | Sigma Aldrich |
| Phthalein purple | 2411-89-4 | | Sigma Aldrich |

At least one of the indicators may be included in the formulation of a drying-type joint compound or any other building construction product which comprises metal ions when wet and which hardens by drying. The drying-type joint compound may comprise a calcium compound which may be calcium carbonate, calcium oxide, calcium sulfate and/or minerals such as gypsum and/or limestone.

In alternative, at least one of the indicators may be added as an accessory product (added before application) to a drying-type joint compound at the time of application and once the joint compound is premixed with water. A particularly preferred formulation for these drying-type joint compounds comprises calconcarboxylic acid as an indicator and at least one calcium compound. A particularly preferred accessory product for these drying-type joint compounds also comprises calconcarboxylic acid as an indicator.

As the applied joint compound comprising a calcium compound dries and a concentration of free calcium ions decreases, the joint compound changes its color. The indicator provides a visual notification to an end user that the applied joint compound is sufficiently dry, and it is prudent to proceed with additional finishing steps. The described formulation serves as manifest, visual indicator of joint compound dryness to both a contractor and amateur end user to facilitate proper finishing and painting of indoor spaces in commercial and residential construction.

One aspect of this disclosure provides a drying-type joint compound which comprises a calcium compound which may be calcium carbonate and a dryness indicator which is an ionochromic dye that detects calcium ions. In addition to or instead of a calcium compound, the drying-type joint compound may comprise a magnesium compound which may be magnesium hydroxide and/or magnesium salts and a dryness indicator which is an ionochromic dye that detects magnesium. In these embodiments comprising a magnesium compound, the ionochromic dye is used which is sensitive to aqueous magnesium.

The drying-type joint compound which comprises at least one ionochromic dye indicator which detects calcium and/or magnesium ions has a first color when mixed with water and is wet. The drying-type joint compound changes to a second color after the drying joint compound has dried. The second color may simply be a decrease or increase in the intensity of the first color. For example, a first color may be purple or red, while the second color may be blue in some embodiments or light purple in other embodiments. The first color and its intensity and the second color and its intensity depend on the amount and chemical structure of the indicator as well as on a concentration of a metal ion to be detected.

Any of the ionochromic dyes that complex with calcium ions may be used as a dryness indicator in these drying-type joint compounds or any other drying building construction products. This includes indicators which are listed in Table 1 and which complex with calcium ions. In some embodiments, at least one of the following indicators or their salts and/or derivatives may be used: calconcarboxylic acid, alizarin, Arsenazo III; phthalein purple and the like, and any combination thereof. A particularly preferred dryness indicator is a reagent which comprises calconcarboxylic acid and/or its derivative and/or its salt. The indicators may be used in any amount sufficient to detect the presence of calcium ions in solution and produce a visible color change once the joint compound has dried. Typically, the indicator is used in an amount from about 0.001% to about 0.5% by weight of the joint compound, including water. In some embodiments, the indicator is used in a range from 1 ppm to 0.5% by weight of the joint compound, including water.

Drying-type joint compounds can be formulated as a dry powder mixture. The dryness indicator may be added to the powder before the powder is packaged for storage and transportation. In these dry mixtures, the dryness indicator also serves as an indicator that the compound stays dry during storage and transportation. Once the joint compound is to be used, it is mixed with water and this produces a visible color change of the joint compound paste. Once the joint compound has dried the color fades away and/or changes to a second color. This provides a visual indication to a user that the applied joint compound has dried.

Drying-type joint compounds can be also formulated as a ready-mixed paste formulation with water. The dryness indicator may be added to the ready-mixed formulation in an amount sufficient to achieve an acceptable first color in the ready-mixed paste. Once the drying-type compound is applied and dries, the first color either fades away and/or changes to a second color. In this application, the dryness indicator also serves as an indicator that a ready-mixed joint compound has not prematurely partially dried during storage and/or transportation.

In further aspects, the dryness indicator may be formulated as an accessory product which is added to a drying-type joint compound at the time of application. A change in color alerts an end user that the drying-type joint compound has dried. This is beneficial for determining whether the applied drying-type joint compound has dried completely. This also alerts the end user if the drying-type joint compound has dried partially in a pail before the drying-type joint compound has been applied.

A particularly preferred drying-type joint compound comprising a dryness indicator is a drying-type joint compound which comprises calconcarboxylic acid and/or its derivative and/or its salt. Sodium sulfate may be added to this formulation.

A particularly preferred accessory dryness indicator product (added before application) for a drying-type joint compound is a reagent which comprises calconcarboxylic acid and/or its derivative and/or its salt. The reagent may also comprise sodium sulfate.

The dryness indicators may be used with any of drying-type joint compounds, dry powder or ready-mixed.

A suitable drying-type joint compound may comprise calcium carbonate and/or any other calcium compound including, but not limited to, calcium oxide, calcium hydroxide, calcium bicarbonate, calcium hypochloride, calcium silicate, calcium nitrate, and calcium chloride. Calcium carbonate may have the highest weight fraction of any ingredient in the joint compound. Calcium carbonate may be present in a form of limestone and/or as any other mineral.

While calcium carbonate has a low-water solubility, a joint compound mixed with water still contains some ionic calcium, while a dry joint compound does not. Other components in the drying-type joint compound may include rheological modifiers, typically cellulosic derivatives, adhesives such as natural or synthetic latexes, water swelling clay minerals such as attapulgite, kaolin, talc, or mica; and binders such as starch derivatives and/or polymeric binders for cohesive properties. Suitable drying-type joint compound formulations are provided in U.S. Pat. Nos. 6,476,099, 6,545,066 and 9,328,023, incorporated herein by reference.

A wet joint compound paste which comprises a dryness indicator comprising calconcarboxylic acid appears purple or red in color, depending on the indicator concentration and grade, and calcium ion concentration, in the presence of aqueous calcium. After the joint compound has dried, its color changes to blue. Calconcarboxylic-acid concentrations sufficient to achieve an acceptable color change to an end user may be in a range from 1 ppm to 0.1% by weight of the total joint compound, water included.

In some embodiments, the color of the joint compound comprising calconcarboxylic acid transitions from lavender to pale sky blue as the joint compound dries. In other embodiments, the color of the joint compound transitions from purple to blue as the joint compound dries. In yet other embodiments, the color of the joint compound transitions from blue to pale sky blue as the joint compound dries.

Setting-type joint compounds possess manifold advantages over drying-type joint compounds in certain applications which require rapid setting, deep fill in patch and repair, and application at lower temperatures.

Setting-type joint compounds and plasters contain calcium sulfate hemihydrate ($CaSO_4 \times 0.5H_2O$), which rapidly rehydrates to gypsum in the presence of water. This hydration reaction is the driver for the setting action in setting-type joint compounds, plasters and other products formulated with calcium sulfate hemihydrate and water, including a gypsum slurry. A typical setting-type joint compound may also comprise any of the following: a filler, rheological modifier, binder, stabilizer and a biocide. Suitable setting-type joint compound formulations are provided in U.S. Pat. Nos. 4,661,161, 5,746,822, 6,805,741 and 9,174,881, which are incorporated herein by reference.

This disclosure provides a setting product which sets via rehydration of calcium sulfate hemihydrate into gypsum in the presence of water. The setting product comprises a setting indicator which comprises an ionochromic dye which is a reversible chelator of calcium ions. The setting indicator may be pre-mixed with the setting product during formulation or the setting indicator may be used as an accessory product which is added to the setting product at the time the setting product is mixed with water and/or activator for application. The setting product may be a setting-type joint compound comprising calcium sulfate hem ihydrate. All types of setting-type joint compounds are contemplated, including a powder setting-type joint compound and a ready-mixed setting-type joint compound.

The setting product may be a gypsum slurry, including gypsum slurries prepared by mixing calcium sulfate hem ihydrate, water and other compounds in order to make a gypsum product such as wallboard, gypsum panels and/or tiles. The setting product may be a plaster, primer coating, or coating.

A setting indicator may comprise calconcarboxylic acid, its derivative or salt. A setting indicator may be any of ionochoromic dyes that complex with calcium and listed in Table 1. A setting indicator may be one of the following ionochromic dyes or their salts and/or derivatives: calconcarboxylic acid, alizarin, arsenazo III; ERIOCHROMR Blue Black R, xylenol orange, calcein, calcein green, calcein blue, zincon, phthalein purple and the like, and any combination thereof. The setting indicator may be used in any concentration sufficient to impart a first color to a setting product in the presence of calcium ions. The first color fades away or is changed to a second color once the setting product has set.

Typically, the setting indicator is used in an amount from about 0.001% to about 0.5% by weight total, including water. For example, if the total weight of a product including water is 100 g, from 0.001 g to 0.5 g of the setting indicator may be used. In some embodiments, the indicator is used in a range from 1 ppm to 0.5% by weight total, including water.

A preferred setting indicator comprises, consists essentially of, consists of calconcarboxylic acid, its salts and derivatives. A particularly preferred setting indicator is calconcarboxylic acid.

Contemplated setting-type joint compounds include ready-mixed setting-type joint compounds. These compounds are pre-mixed with water and comprise at least one retarder which blocks a setting reaction by reversibly binding calcium until a setting activator is added during application. A retarder may be a proteinaceous retarder, a low molecular weight polyacrylate and/or non-calcium bearing phosphate. Typically, a retarder is a strong chelating agent such as tetrapotassium pyrophosphate (TKPP), tetrasodium pyrophosphate (TSPP), sodium citrate, among others. Other suitable retarders in this group include zinc hexametaphosphate, potassium tripolyphosphate, sodium tripolyphosphate, mono-ammonium phosphate, monobasic potassium phosphate and any mixtures thereof.

A setting activator which is also referred interchangeably as an accelerator is added to a ready-mixed setting-type joint compound at the time of use in order to trigger a setting reaction of calcium sulfate hem ihydrate. This allows calcium sulfate hem ihydrate to rehydrate and the compound to harden.

Suitable activators include zinc compounds, in particularly zinc sulfate and/or any of zinc sulfate hydrates; aluminum compounds, including aluminum salts such as aluminum sulfate, aluminum ammonium sulfate, and aluminum potassium sulfate; and any combinations thereof. A setting time can be modulated by varying an amount of accelerator added. Suitable activators and inhibitors are provided in U.S. Pat. No. 5,746,822, incorporated herein by reference.

A setting indicator is incorporated into a setting-type joint compound or plaster formulation, with a color transition indicating the onset of the setting action. In the presence of sufficient amounts of retarder, the calcium cation is chelated, and the ionochromic dye exhibits first color. Upon addition of a sufficient amount of activator, the first color changes abruptly into a second color. As the setting-type compound, gypsum slurry or plaster rehydrates and hardens, the second color intensity gradually diminishes.

Changes in color in a setting-type joint compound, plaster or any other gypsum setting product which comprise a setting indicator serves as a visual cue to the end user, e.g. the contractor or homeowner, of an onset of the setting action. Furthermore, it indicates that sufficient amounts of a retarder or activator have been incorporated into the product. Additionally, the color intensity after addition of an activator may function as an estimate of setting or workability time also known as an open time which is the time until the product has hardened and no longer may be applied.

A setting indicator may be incorporated into a setting-type joint compound or plaster formulation in the presence of a retarder. The weight fraction of the setting indicator ranges from 0.001%-1% on a dry basis of the compound total.

Before addition of any accelerator, a ready-mixed setting-type compound or plaster is of a first color, e.g. blue if a reagent comprising calconcarboxylic acid is used as a setting indicator. If an activator is added in an amount sufficient to induce a setting action, the first color of the joint compound or plaster changes abruptly to a second color, e.g. into red or purple with calconcarboxylic acid as an indicator. As the setting-type compound or plaster sets or undergoes drying to completion, the second color becomes gradually lighter or it changes to a third color, e.g. light pink with calconcarboxylic acid. Thus, a setting indicator may be used to monitor an open time during setting, completion of a setting reaction and cure, as well as to monitor a ready-mixed joint compound during storage and transportation for premature onset of setting.

If an activator is not added in an optimum amount to trigger a setting reaction sufficiently, the first color will not transition completely into the second color. This may be used as a rapid and accurate method for optimization of a setting reaction during application of a joint compound.

The color intensity may be more robust with more accelerator, serving as a method to qualify a setting time, i.e. a second color in a setting-type joint compound that sets in 10 minutes appears more intense, i.e. darker red if calconcarboxylic acid is used as an indication, than a setting-type joint compound that sets in 20 minutes.

While some ready-mixed setting-type joint compounds are formulated with a setting indicator during manufacturing, other applications include a ready-mixed setting-type joint compound to which a setting indicator is added at the same time when a setting reaction is triggered with an activator.

A setting-type joint compound, plaster or a gypsum slurry is prepared by mixing together calcined gypsum and water. Any of these formulations may also comprise one or more from the following components: a dispenser, surfactant, defoamer, binder, filler, biocide, retarder, activator, stabilizer. Some of these components may be first mixed with water and then mixed with dry ingredients including calcined gypsum. In some embodiments, the setting indicator is incorporated into water together with a dispersant and defoamer. In other embodiments, the setting indicator is incorporated immediately after water, a binder, retarder and biocide, but before addition of the remainder of dry ingredients. In further embodiments, the setting indicator may be added after all other ingredients have been mixed. The setting indicator may be used in formulation with or without defoamer, dispersant and with or without an activator.

An indicator either of a drying or setting reaction may be formulated as an accessory product which is added to a product such as a drying-type joint compound, a setting-type joint compound, a plaster, a coating, a primer coating or a gypsum slurry at the time of application.

An accessory product comprising an indicator may be provided in a separate package. The amount of the indicator may be dosed such that no additional measurements are needed during mixing with a joint compound. The package may be of any shape. It may be a container, a pre-filled syringe and/or bottle. A flexible bag or pouch is particularly preferred. If a package may provide the indicator in predetermined dosages. The package may comprise several compartments, each compartment containing a predetermined dosage of the indicator. A predetermined dosage may be calculated as the dosage needed to produce a color change in a particular volume of a joint compound (i.e. one gallon, including water) or any other product for monitoring a setting or drying reaction of which the indicator is to be used.

During application of an accessory product comprising the indicator, a user may easily use one or several dosages of the indicator, depending on the amount of a product to be monitored.

The indicator in the package may be formulated as a powder or as a paste pre-mixed with a solvent which may be water or an organic solvent. Other components in the accessory product may include a stabilizer and/or a carrier.

The indicator such as calconcarboxylic acid may be premixed with a carrier in a solution. The mixture is then allowed to evaporate, producing a carrier coated with the indicator. Suitable carriers include any calcium compound, talc, sodium salt, e.g. sodium chloride or sodium sulfate, and/or magnesium salt. Calcium carbonate and gypsum are particularly preferred compounds. A carrier may be a filler (i.e. talc or mica) commonly used in a gypsum product. These indicator formulations which comprise a mixture of an indicator with a carrier may be used either as an accessory product or they may be also used in any other applications in order in improve mixing of an indicator with a joint compound or any other product a setting or drying reaction of which is to be monitored with an indicator.

Various methods may be used in order to detect changes in color of a product. Some indicators such as based on calconcarboxylic acid, its derivative or salt produce a change in color which is easily detected by a human eye. Other formulations may comprise an indicator which is a fluorescent dye which is to be detected with a UV lamp or some other equipment.

Color differences in the formulations of the present disclosure may be also measured more precisely by the L*a*b* method. This method employs a colorimeter such as for example ColorQUESTR from HunterLab. The L*a*b* method allows for the detection of even slight differences between two colors. In the L*a*b* method, color difference is defined as a numerical comparison of a sample's color to a standard. Three different coordinates are used:

L* indicates lightness (black/white), with L*=100 being pure white and L*=0 being pure black;

a* is the red/green coordinate, with a*=−100 being perfectly green, and a*=100 being perfectly red, and b* is the yellow/blue coordinate, with b*=100 being perfectly yellow and b*=−100 being perfectly blue.

All measurements are conducted against standards provided with a colorimeter for each coordinate.

Each of two samples are measured for L*, a* and b*. Delta E is then calculated as follows:

$$\Delta E = \sqrt{(L^*_1 - L^*_2)^2 + (a^*_1 - a^*_2)^2 + (b^*_1 - b^*_2)^2}$$

Delta E represents a difference in color between the first sample and a second sample. Most humans can easily detect a color change between two colors if delta E between these two colors is 3 or higher. An experienced user is able to detect a change in color which is as low as 0.5-1.

EXAMPLE 1

A lightweight ready-mixed drying-type joint compound which comprised calcium carbonate was formulated with calconcarboxylic acid in the amount of 0.01% by weight of the joint compound, including water. The color of the compound was blue/lavender. The color changed to sky blue once the compound dried.

The color of the compound when wet and dry was also examined by the L*a*b* method. The wet state color was measured at the time of application. The dry state color was measured more than 24 hours after the application. The results are reported in Table 2 below:

TABLE 2

|  | L* | A* | B* |
|---|---|---|---|
| Wet | 69.0 | −5.2 | −4.2 |
| Dry | 72.9 | −2.7 | −1.7 |
| Delta E |  | 5.3 |  |

EXAMPLE 2

A setting reaction was studied in a ready-mixed setting-type joint compound with various amounts of an indicator (calconcarboxylic acid) and activator. The compound comprised calcined gypsum with inhibitor. The indicator was added to the compound in an amount in the range from 0.005% to 0.010% by weight of the composition total, including water. The color of the compound was blue. An activator (a mixture of zinc sulfate and alum) was then added in an amount in the range from 1.0% to 1.5% by weight of the composition total, including water. Once the activator was added, the color of the compound changed to red/pink. Once the compound was fully set, the color faded to light pink.

The color of the compounds when wet and set was also examined by the L*a*b* method. The results are reported in FIGS. 1-4.

FIG. 1 is a scatterplot of L* values versus time (in minutes) after the activator has been added.

Figure 2:
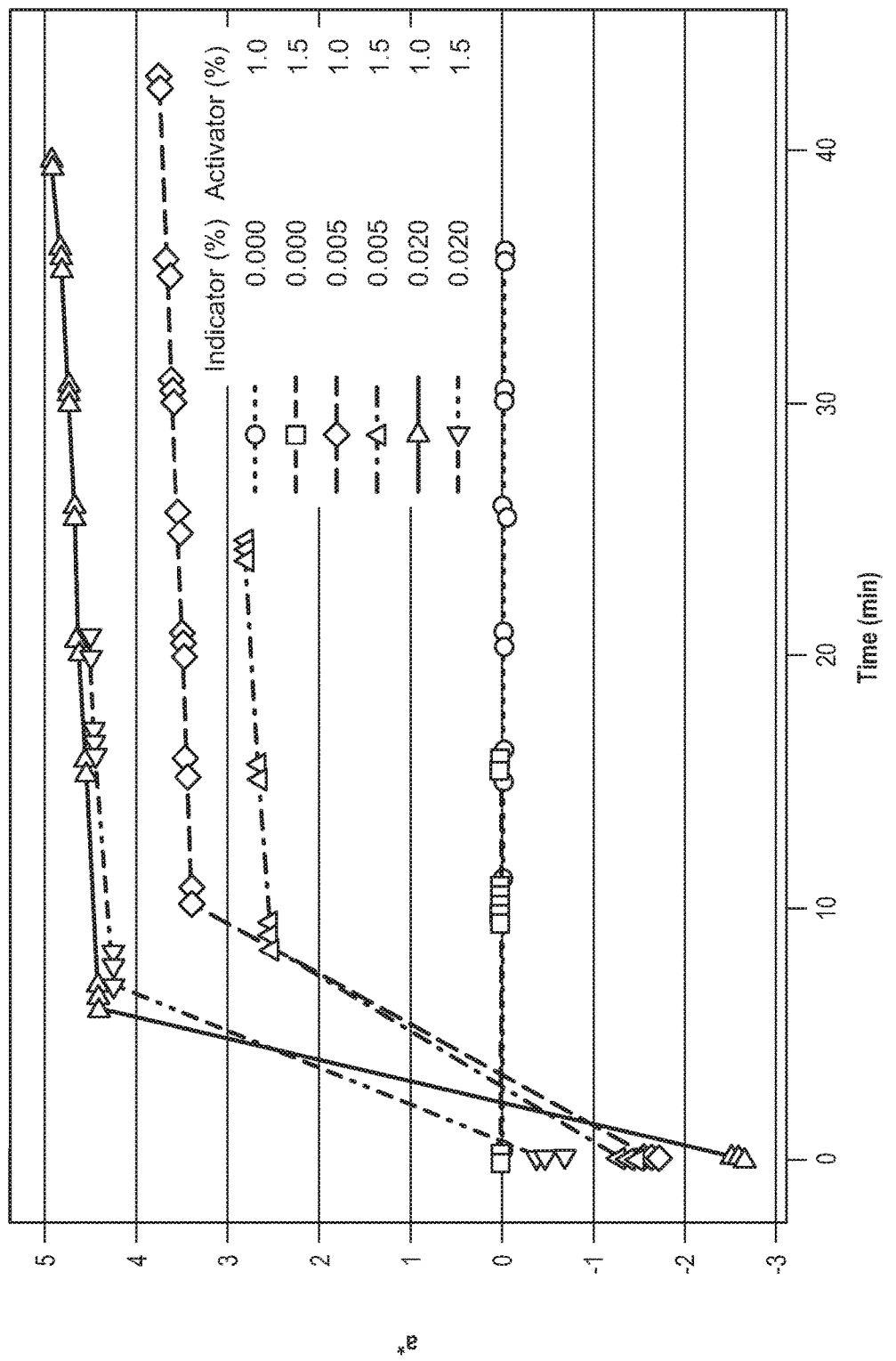
FIG. 2 are graphs of A* value as a function of time for a setting-type joint compound in a ready-mixed state with varying amounts of an indicator and activator.

FIG. 2 is a scatterplot of a* values versus time (in minutes) after the activator has been added.

Figure 3:
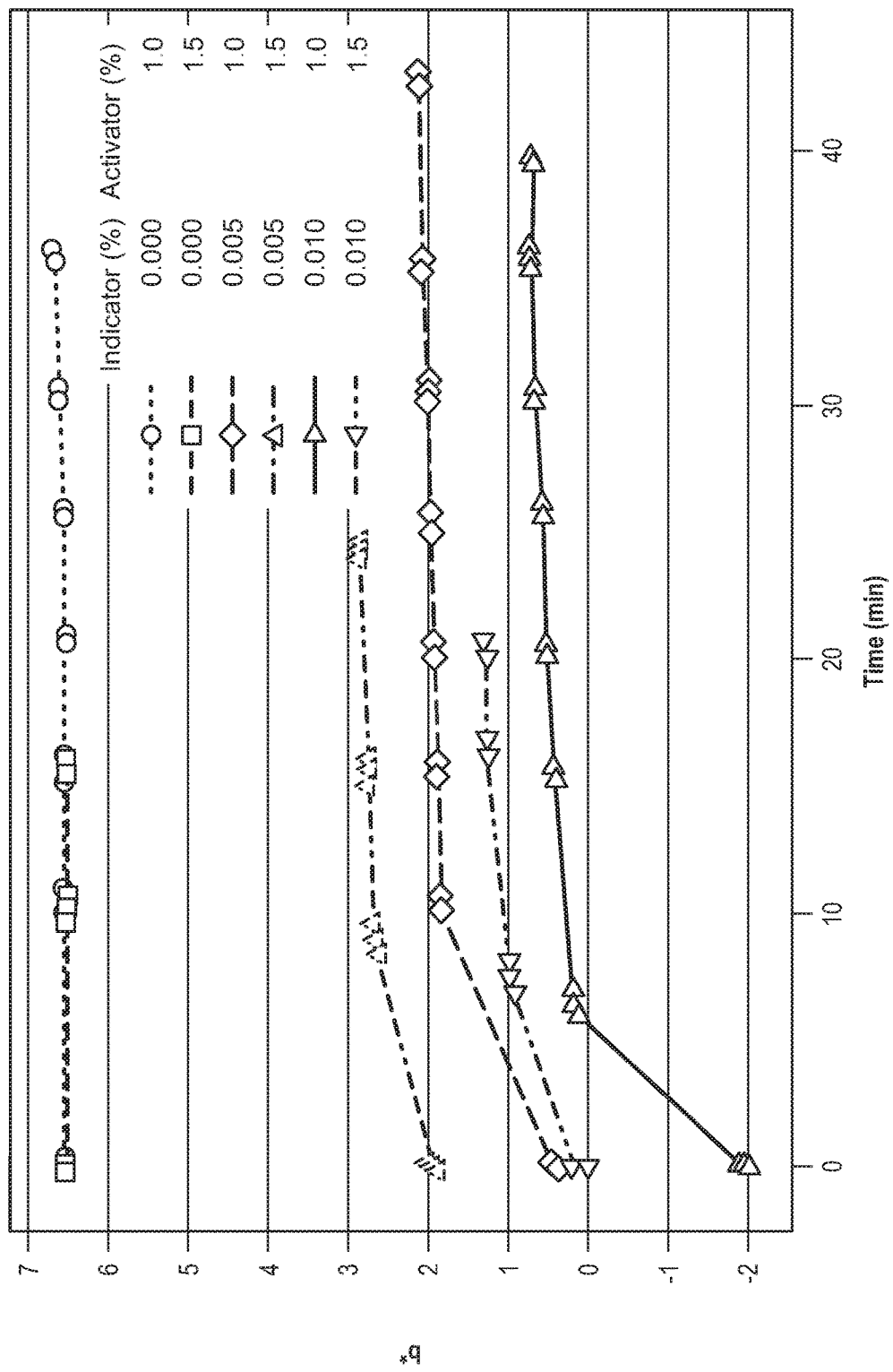
FIG. 3 are graphs of B* value as a function of time for a setting-type joint compound in a ready-mixed state with varying amounts of an indicator and activator.

FIG. 3 is a scatterplot of b* values versus time (in minutes) after the activator has been added.

Figure 4:
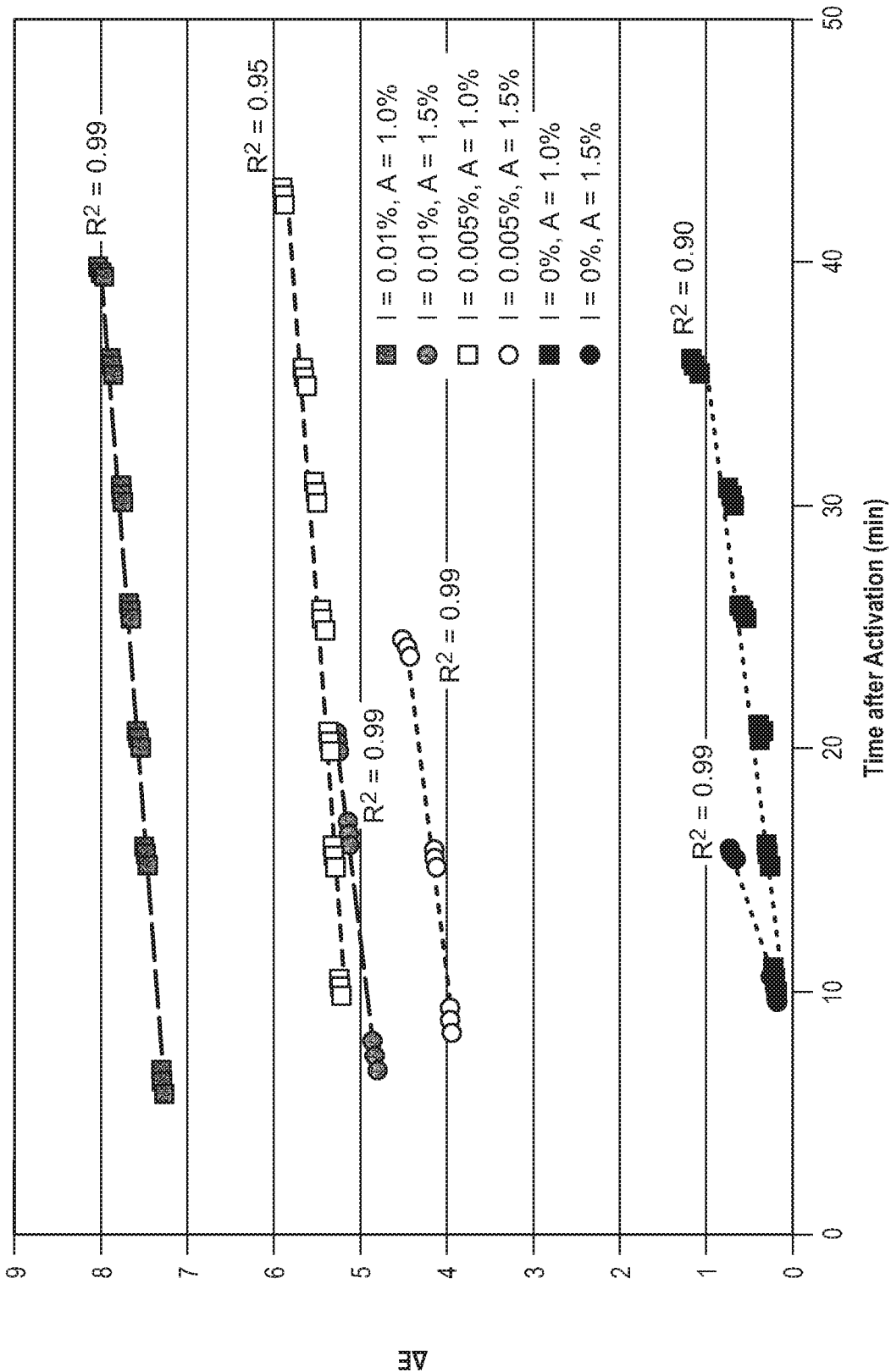
FIG. 4 are ΔE calculated after addition of an activator as a function of time for a setting-type joint compound in a ready-mixed state with varying amounts of an indicator and activator.

FIG. 4 reports delta E values calculated after the addition of an activator as a function of time for a setting-type joint compound with varying amounts of indicator and activator.

EXAMPLE 3

In order to produce an indicator coated on a carrier, 1 g of calconcarboxylic acid was mixed with 99 g of talc or sodium chloride, and water. The mixture was boiled and water was allowed to evaporate. The resulting solid product was calconcarboxylic acid coated on a carrier. A mortar or pestle was used to grind the resulting solid product into fine powder.

What is claimed is:

1. A building construction product comprising calconcarboxylic acid and/or a salt of calconcarboxylic acid, wherein the product is a gypsum slurry, plaster or a setting-type joint compound comprising a non-calcium bearing phosphate, and wherein the building construction product sets by a setting reaction in which calcium sulfate hemihydrate hydrates to gypsum, and wherein the calconcarboxylic acid and/or the salt of calconcarboxylic acid is present in the building construction product in an amount sufficient for producing a visibly detectable color change in the building construction product which has set and hardened, and wherein the visibly detectable color change is indicative of the building construction product being set and hardened.

2. The building construction product of claim 1, wherein the calconcarboxylic acid is coated on a carrier, and wherein the calconcarboxylic acid coated on the carrier is obtained by:
   a) mixing calconcarboxylic acid with talc or sodium chloride and water,
   b) boiling the mixture and evaporating water and thereby producing a solid product; and
   c) grinding the solid product into a powder.

3. The building construction product of claim 1, wherein the product is a ready-mixed setting-type joint compound which further comprises a proteinaceous retarder, and/or a low molecular weight polyacrylate.

4. The building construction product of claim 1, wherein calconcarboxylic acid is in an amount from about 0.001% to about 0.5% by weight.

5. The building construction product of claim 1, wherein the building construction product is the setting-type joint compound which is ready-mixed with water and comprises a non-calcium bearing phosphate, and wherein the building construction product sets and hardens by adding to the ready-mixed setting-type joint compound an activator comprising zinc sulfate, alum or any combination thereof.

6. The building construction product of claim 5, wherein the activator is added an amount in the range from 1.0% to 1.5% by weight.

7. The building construction product of claim 5, wherein the calconcarboxylic acid and/or the salt of calconcarboxylic acid is in an amount in the range from 0.005% to 0.010% by weight.

* * * * *